US00PP36288P2

(12) United States Plant Patent
Knoblauch

(10) Patent No.: US PP36,288 P2
(45) Date of Patent: Dec. 3, 2024

(54) ***BEGONIA* PLANT NAMED 'BEYZ0002'**

(50) Latin Name: *Begonia hybrida*
Varietal Denomination: BEYZ0002

(71) Applicant: SYNGENTA CROP PROTECTION AG, Basel (CH)

(72) Inventor: Cathy Knoblauch, Whitecourt (CA)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 18/445,781

(22) Filed: Jan. 30, 2024

(51) Int. Cl.
*A01H 5/02* (2018.01)
*A01H 6/18* (2018.01)

(52) U.S. Cl.
USPC ..... Plt./343
CPC ..... *A01H 6/185* (2018.05)

(58) Field of Classification Search
USPC ..... Plt./343
CPC ..... A01H 6/185; A01H 5/02
See application file for complete search history.

*Primary Examiner* — Keith O. Robinson
(74) *Attorney, Agent, or Firm* — Dale Skalla

(57) ABSTRACT

A new *Begonia* plant named 'BEYZ0002' characterized by its compact, symmetrical and rounded habit, double white flowers that bloom continuously from spring until fall, prolific and continuous basal branching and foliage that is very dark, glosssy and mahogany in color with bright green contrasting veins.

1 Drawing Sheet

Figure 1:
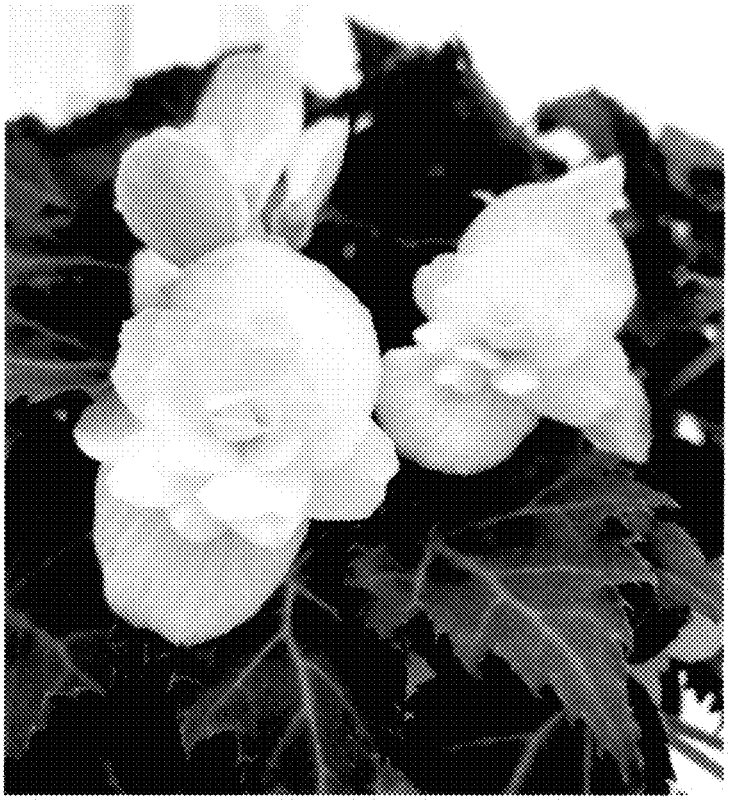

Latin name of the genus and species of the plant claimed: *Begonia hybrida.*

Varietal denomination: 'BEYZ0002'.

BACKGROUND OF THE NEW PLANT

The present invention comprises a new *Begonia* plant, botanically known as *Begonia hybrida*, and hereinafter referred to by the variety name 'BEYZ0002'. 'BEYZ0002' is a product of a planned breeding program in Whitecourt, Alberta, Canada. The new cultivar 'BEYZ0002' has compact, symmetrical and rounded habit, double white flowers that bloom continuously from spring until fall, continuous basal branching and foliage that is dark, glossy and mahogany in color with bright green contrasting veins.

The new *Begonia* cultivar, 'BEYZ0002', is the result of a planned pollination conducted at the inventor's nursery made in August 2018. The female parent of the new cultivar is the unnamed white seedling, of proprietary origin, unpatented, characterized by its larger flowers and leaves. 'BEYZ0002' differs from unnamed white seedling of the inventor's proprietary selection, unpatented by having a smaller flower and leaf size.

The male parent of the new cultivar is the unnamed seedling of proprietary selection, unpatented, having a smaller overall plant habit than 'BEYZ0002'. The resulting seed was sown in Whitecourt, Alberta, Canada in a controlled greenhouse environment in 2018 and 'BEYZ0002' was selected as one flowering plant within the progeny of the stated cross in May 2019.

The first act of asexual reproduction of 'BEYZ0002' was accomplished when vegetative tip cuttings were propagated from the initial selection in May 2019 at the inventor's nursery in May 2018 in Whitecourt, Alberta, Canada.

BRIEF SUMMARY OF INVENTION

Plants of the new *Begonia* have not been observed under all possible combinations of environmental conditions and cultural practices. The phenotype may vary somewhat with variations in environmental conditions such as temperature and light intensity, without, however, any variance in genotype.

A Plant Breeder's Right for this cultivar has not yet been applied for. 'BEYZ0002' has not been made publicly available prior to the effective filing date of this application, notwithstanding any disclosure that may have been made less than one year prior to the effective filing date of this application by the inventor or another who obtained directly from the inventor.

The following traits have been repeatedly observed and are determined to be basic characteristics of the new variety. The combination of these characteristics distinguishes this *Begonia* as a new and distinct variety.

1. 'BEYZ0002' has a compact, symmetrical and freely branching habit.
2. 'BEYZ0002' flowers naturally and continually from spring to fall.
3. 'BEYZ0002' exhibits continuous basal branching.
4. 'BEYZ0002' achieves a height of 25 cm high and 30 cm wide in one season grown in a one gallon pot in the greenhouse.

BRIEF DESCRIPTION OF THE PHOTOGRAPHS

The accompanying photographic drawings show typical flower and foliage characteristics of 'BEYZ0002' with colors being as true as possible with an illustration of this type.

Figure 2:
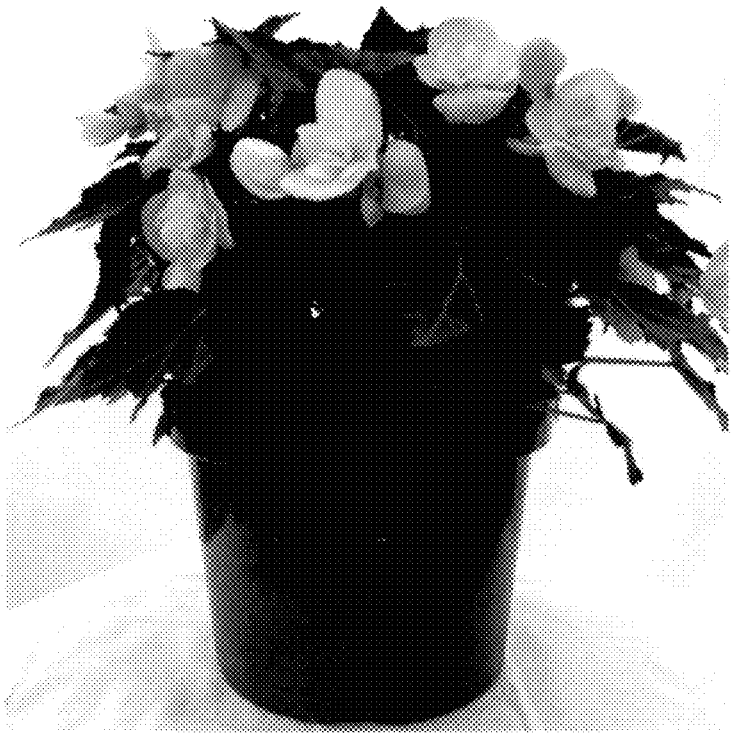

The photographic drawings show in FIG. 1 a close view of an inflorescence taken in Whitecourt, Alberta, Canada in August 2023, and in FIG. 2 a whole flowering plant taken in Whitecourt, Alberta, Canada in August 2023. The plant in the photographic drawings is 16 weeks old and is in an 8" pot. The plant was grown at the inventor's greenhouse, under natural light in Whitecourt, Alberta, Canada during the summer of 2023.

DETAILED BOTANICAL DESCRIPTION

The plant descriptions and measurements were taken in Whitecourt, Alberta, Canada in August 2023. The plants were approximately 6 months old and were growing in 8 inch pots, one plant per pot, in a greenhouse.

Color references are made to The Royal Horticultural Society Colour Chart (R.H.S.) 2001.

TABLE 1

DIFFERENCES BETWEEN THE NEW VARIETY 'BEZY0002' AND A MOST SIMILAR VARIETY

| | 'BEYZ0002' | 'Mocha White', Not patented |
|---|---|---|
| Flower and leaf size: | Smaller | Larger |
| Foliage: | Smooth, glossy, and glabrous | Pubescent |
| Basal and lateral branching: | Natural and prolific | Limited branching and an asymmetrical habit |

Propagation:
- *Type*.—Vegetative tip cuttings.
- *Time to initiate roots, summer and winter*.—Summer 15 days, Winter 20 days.
- *Time to produce a rooted young plant summer*.—35 days.
- *Time to produce a rooted young plant, winter*.—40 days.
- *Root description*.—Medium thin.
- *Rooting habit*.—Freely branching.

Plant description:
- *Plant and growth habit*.—Upright, mounded and freely branching.
- *Plant height, soil level to top of foliar plane*.—About 22 cm.
- *Plant height, soil level to top of floral plane*.—About 26 cm.
- *Plant width*.—About 25 cm.
- *Lateral branch description*.—Upright, freely branched.
- *Length*.—About 15 cm.
- *Diameter*.—About 5 mm.
- *Internode length*.—About 3 cm.
- *Strength*.—Moderately strong.
- *Aspect*.—Upright, symmetrical.
- *Texture and luster*.—Smooth, glossy.
- *Leaf color, developing*.—Nearest RHS 152C.
- *Leaf color, developed*.—RHS 200B.

Leaf description:
- *Arrangement*.—Alternate.
- *Length*.—About 9 cm.
- *Width*.—About 5 cm.
- *Shape*.—Cordate, asymmetrical.
- *Apex*.—Sharply acute.
- *Base*.—Cordate.
- *Margin*.—Double serrate.
- *Texture and luster, upper and lower surfaces*.—Glabrous, glossy.
- *Color, upper surfaces*.—About RHS 200B.
- *Color, lower surfaces*.—About RHS 46A.
- *Venation pattern*.—
  - *Developing leaves, upper surface*.—Palmate-pinnate.
  - *Developing leaves, lower surface*.—Palmate-pinnate.
  - *Fully expanded leaves, upper surface*.—Palmate-pinnate.
  - *Fully expanded leaves, lower surface*.—Palmate-pinnate.

Petioles:
- *Length*.—About 5-7 cm.
- *Diameter*.—About 3 mm.
- *Texture and luster, upper and lower surfaces*.—Glabrous, smooth, glossy.
- *Strength*.—Moderately strong, wiry.
- *Color, upper surface*.—Nearest RHS 177A.
- *Color, lower surface*.—Nearest RHS 175A.

Stipules:
- *Quantity per leaf*.—2, opposite.
- *Length*.—5 mm.
- *Width*.—5 mm.
- *Shape*.—Triangular.
- *Apex*.—Sharply acute.
- *Base*.—Truncate.
- *Margins*.—Entire.
- *Color, upper and lower surfaces*.—Nearest RHS 196C.

Flower description:
- *Flowering habit*.—Continuous.
- *Fragrance*.—None.
- *Natural flowering season*.—Spring to fall.
- *Flower longevity*.—About 30 days.
- *Inflorescence height (including peduncle)*.—About 9 cm.

Female flowers:
- *Buds, width*.—About 2 cm.
- *Buds, length*.—About 2.3 cm.
- *Diameter, flattened*.—About 2.5 cm.
- *Shape*.—Flattened, ovoid.
- *Texture and luster*.—Smooth, matte.
- *Color, when opening, upper surface*.—Nearest RHS 155C.
- *Color, when opening, lower surface*.—Nearest RHS 155C.
- *Color, when fully opened, upper surface*.—Nearest RHS 155C.
- *Color, when fully opened, lower surface*.—Nearest RHS 155C.
- *Size, length*.—About 5 cm.
- *Size, width*.—About 5 cm.
- *Tepaloids*.—None observed.

Tepals:
- *Quantity per flower and arrangement*.—5 arranged in a single whorl.
- *Length*.—About 2.5 cm.
- *Width*.—About 2.5 cm.
- *Shape*.—Ovate.
- *Apex*.—Broadly ovate.
- *Base*.—Broadly ovate.
- *Margin*.—Entire.
- *Texture and luster, upper surface*.—Smooth, matte.
- *Texture and luster lower surface*.—Smooth, matte.
- *Color, tepals*.—
  - *When opening, upper surface*.—Nearest RHS 155C.
  - *When opening, lower surface*.—Nearest RHS 155C.
  - *Fully opened, upper surface*.—Nearest RHS 155C.
  - *Fully opened, lower surface*.—Nearest RHS 155C.
  - *Tepaloids*.—None observed.

Pedicels, female flowers:
*Length*.—About 1.5 cm.
*Diameter*.—2 mm.
*Angle*.—About 45 degrees.
*Strength*.—Moderate.
*Texture and luster*.—Smooth, glossy.
*Color, upper surface*.—Nearest RHS 157B.
*Color, lower surface*.—Nearest RHS 157B.
*Reproductive organs*.—
*Gynoecium*.—
*Quantity per flower*.—One.
*Pistil length*.—1.5 mm.
*Stigma diameter*.—1 mm.
*Stigma shape*.—Bifurcated, loose spiral.
*Stigma color*.—RHS 160C.
*Style length*.—1.5 mm.
*Style color*.—Nearest RHS 160D.
*Ovary color*.—Nearest RHS 160B.
*Seeds and fruits*.—None observed.

Male flowers:
*Size, width*.—About 4 cm.
*Size, length*.—About 5 cm.

Tepals:
*Quantity per flower and arrangement*.—About 15-20 arranged in about three whorls.
*Length, inner tepals*.—About 1.5 cm.
*Length, outer tepals*.—About 3 cm.
*Width, inner tepals*.—About 1 cm.
*Width, outer tepals*.—About 2.2 cm.
*Shape, inner tepals*.—Ovoid.
*Shape, outer tepals*.—Broadly ovate.
*Apex, inner and outer tepals*.—Broadly ovate.
*Base, inner and outer tepals*.—Broadly ovate.
*Margin, inner and outer tepals*.—Smooth, entire.
*Texture and luster, inner and outer tepals, upper surface*.—Smooth, matte.
*Texture and luster, inner and outer tepals, lower surface*.—Smooth, matte.
*Color, inner tepals*.—
*When opening, upper surface*.—Nearest RHS 155C.
*When opening, lower surface*.—Nearest RHS 155C.
*Fully opened, upper and lower surfaces*.—Nearest RHS 155C.
*Color, outer tepals*.—
*When opening, upper surface*.—Nearest RHS 155C.
*When opening, lower surface*.—Nearest RHS 155C.
*Fully opened, upper surface*.—Nearest RHS 155C.
*Fully opened, lower surface*.—Nearest RHS 155C.
*Tepaloids*.—None observed on male flowers.

Peduncles, male flowers:
*Length*.—About 5 cm.
*Diameter*.—About 3 mm.
*Angle*.—Mostly upright.
*Strength*.—Moderately strong.
*Texture and luster*.—Smooth, glossy.
*Color, upper and lower surfaces*.—Nearest RHS 164B.

Pedicels, male flowers:
*Length*.—About 1.5 cm.
*Diameter*.—2 mm.
*Angle*.—Upright.
*Strength*.—Moderate.
*Texture and luster*.—Smooth, glossy.
*Color, upper and lower surfaces*.—Nearest RHS 164B.
*Color, upper surface*.—Nearest RHS 158A.
*Color, lower surface*.—Nearest RHS 158A.

Flower bracts:
*Quantity per flower and arrangement*.—2, opposite.
*Length*.—9 mm.
*Width*.—9 mm.
*Shape*.—Ovate.
*Apex*.—Roundly obtuse.
*Base*.—Obtuse.
*Margin*.—Entire, ciliate.
*Texture and luster, upper and lower surfaces*.—Smooth, glossy.
*Color, upper and lower surfaces*.—Nearest RHS 157A.

Reproductive organs:
*Androecium*.—Sterile.
*Stamen quantity per flower*.—None.
*Filament length*.—None.
*Filament color*.—None.
*Anther size*.—None.
*Anther shape*.—None.
*Anther color*.—None.
*Amount of pollen*.—None.
*Pollen color*.—None.

Pathogen & pest resistance: To date, resistance to pathogens and pests common to *Begonia* plants has not been observed on plants of the new *Begonia*.

Temperature tolerance: Plants of the new *Begonia* have been observed to tolerate high temperatures of about 30° C. and to be suitable for USDA Hardiness Zones 7 to 9.

What is claimed is:

1. A new and distinct variety of *Begonia* plant named 'BEYZ0002' substantially as illustrated and described herein.

* * * * *